United States Patent [19]

Fung et al.

[11] Patent Number: 5,908,941

[45] Date of Patent: Jun. 1, 1999

[54] METHOD OF SYNTHESIZING GAMMA PYRONES

[75] Inventors: Fu-Ning Fung, Salem; Bruce A. Hay, Groton; James E. Swenarton, deceased, late of Waterford, all of Conn., by Ellen E. Swenarton, legal representative

[73] Assignee: Cultor, Ltd., Helsinki, Finland

[21] Appl. No.: 08/676,230

[22] PCT Filed: Dec. 16, 1994

[86] PCT No.: PCT/IB94/00432

§ 371 Date: Nov. 6, 1996

§ 102(e) Date: Nov. 6, 1996

[87] PCT Pub. No.: WO95/20584

PCT Pub. Date: Aug. 3, 1995

[51] Int. Cl.[6] .................................................. C07D 315/00
[52] U.S. Cl. ........................................... 549/417; 549/418
[58] Field of Search ...................................... 549/419, 418

[56] References Cited

U.S. PATENT DOCUMENTS

| | | | |
|---|---|---|---|
| 4,126,624 | 11/1978 | Brennan et al. | 260/345.9 |
| 4,342,697 | 8/1982 | Weeks et al. | 549/396 |
| 4,390,709 | 6/1983 | Weeks et al. | 549/418 |
| 4,435,584 | 3/1984 | Brennan et al. | 549/415 |
| 4,451,661 | 5/1984 | Weeks et al. | 549/417 |

OTHER PUBLICATIONS

Weeks et a l., J. Org. Chem., 1980, 45, pp. 1109–1113.

Harada et al., Agric. Biol. Chem., 47(12), pp. 2921–2922, 1983.

*Primary Examiner*—John Kight
*Assistant Examiner*—Raymond Covington

[57] ABSTRACT

Maltol and ethyl maltol can be produced from a haloenone intermediate by reacting the intermediate with acid in a reaction medium comprising an aprotic solvent.

18 Claims, No Drawings

METHOD OF SYNTHESIZING GAMMA PYRONES

This application is a 371 of PCT/IB94/00432 filed Dec. 16, 1994.

FIELD OF THE INVENTION

This invention relates to a process for producing certain gamma pyrones such as maltol and ethyl maltol, which process is characterized by the use of a dry aprotic solvent as a reaction medium.

BACKGROUND OF THE INVENTION

Maltol is a naturally occurring substance found in the bark of young larch trees, pine needles and chicory. Maltol has the structure

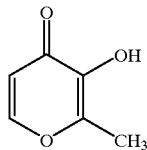

(I)

Maltol is one of a family of compounds called gamma pyrones which enhance the flavor and aroma of a variety of food products and which, in general, have the formula

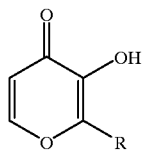

(II)

wherein R is hydrogen, $(C_1-C_6)$alkyl, $(C_2-C_6)$alkenyl, phenyl, or benzyl. The compounds wherein R is methyl (maltol) or ethyl (ethyl maltol) are regulated for use as flavor enhancers in foods. In addition, these materials are used as ingredients in perfumes and essences. Pyromeconic acid (formula II, R=H) derivatives such as the 2-alkenylpyromeconic acids reported in U.S. Pat. No. 3,365,469 inhibit the growth of bacteria and fungi and are useful as flavor and aroma enhancers in foods and beverages and aroma enhancers in perfumes.

Many processes for producing maltol have been reported. Early commercial production was from the destructive distillation of wood. Synthesis of maltol from 3-hydroxy-2-(1-piperidylmethyl)-1,4-pyrone was reported by Spielman and Freifelder in J. Am. Chem. Soc., 69, 2908 (1947). Schenck and Spielman, J. Am. Chem. Soc., 67, 2276 (1945), obtained maltol by alkaline hydrolysis of streptomycin salts. Chawla and McGonigal, J. Org. Chem., 39, 3281 (1974) and Lichtenthaler and Heidel, Angew. Chem., 81, 998 (1969), reported the synthesis of maltol from protected carbohydrate derivatives. Shono and Matsumura, Tetrahedron Letters No. 17, 1363 (1976), described a five step synthesis of maltol starting with methyl furfuryl alcohol.

Syntheses of gamma-pyrones such as pyromeconic acid, maltol, ethyl maltol and other 2-substituted-3-hydroxy-gamma-pyrones are described in U.S. Pat. Nos. 3,130,204; 3,133,089; 3,140,239; 3,159,652; 3,365,469; 3,376,317; 3,468,915; 3,440,183; 3,446,629; 4,082,717; 4,147,705; 4,323,506; 4,342,697; 4,387,235; 4,390,709; 4,435,584; and 4,451,661. A typical process for making gamma pyrones is illustrated by U.S. Pat. No. 4,435,584 to Brennan et al. This patent describes a one pot, furfuryl alcohol based synthesis wherein all reactions are conducted in aqueous/protic media. The present invention is based on chemistry which can employ a furfuryl alcohol precursor, but which, by contrast, employs a reaction medium comprising an aprotic solvent to effect the conversion of a haloenone to the desired gamma pyrone product.

U.S. Pat. No. 4,126,624 discloses preparation of gamma-pyrones from 3-substituted furans by procedures which can employ isolation of various components by extraction with various organic solvents.

SUMMARY OF THE INVENTION

This invention, in one aspect, provides a method of synthesizing compounds having the formula

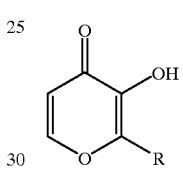

(II)

wherein R is $(C_1-C_6)$alkyl, $(C_2-C_6)$alkenyl, phenyl, or benzyl, comprising treating, at a temperature above about 40° C., preferably above about 60° C., and in a reaction medium comprising an aprotic solvent, a compound (a haloenone) having the formula

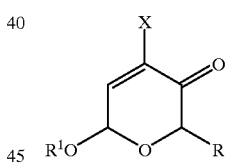

(III)

wherein R is as defined above, $R^1$ is $(C_1-C_6)$alkyl or hydroxy$(C_2-C_4)$alkyl, and X is chloro or bromo, with a catalytically effective amount of acid, thereby effecting conversion of said compound III to said compound II. While temperatures as high as 200° C. or higher can be employed, it is most preferred to conduct the reaction at a temperature within the range of about 80° C. to about 120° C.

The above discussion illustrates a reaction in which haloenone III is converted to gamma pyrone II. The acronym "H-T-GP" is herein employed as an abbreviation for the phrase "haloenone-to-gamma pyrone" for convenience.

A haloenone of formula III can be generated by reacting a corresponding furfuryl alcohol of formula IV, with a halogen oxidant and in an aqueous solution of an alcohol, $R^1OH$, as illustrated by scheme I following, which also displays the penultimate H-T-GP conversion step discussed above, and thus illustrates an overall process for making compounds according to this invention.

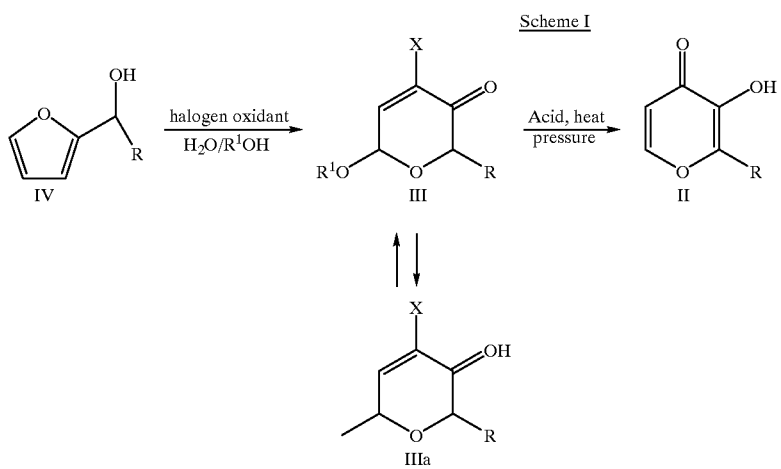

Scheme I

It is noted that the alkoxy form of haloenone III is believed to be in equilibrium with, among other species, hydroxy form IIIa, the equilibrium being referred to below as the "alkoxy-hydroxy equilibrium".

Precursor compounds useful as starting materials in making furfuryl alcohols of formula IV are well known in this art together with processes for making the alcohols. Compounds of formula IV can be made, for example, by reacting furfural with an appropriate corresponding Gringard reagent of formula RMgX where R and X are as previously defined. A number of furfuryl alcohols useful in this invention may also be purchased commercially.

It is conventional to conduct both the first step of Scheme I, in which furfuryl alcohol IV is converted to haloenone III (this first step herein being abbreviated herein as the "ATH conversion", with "ATH" being an acronym for "alcohol-to-haloenone") and the second H-T-GP conversion step, in which haloenone III is converted to gamma pyrone II (this second step herein being abbreviated as the "H-T-GP conversion") in a solvent which is a mixture of water and a $(C_1–C_6)$alcohol, usually methanol or ethanol, or a $(C_2–C_4)$ diol such as ethylene glycol, propylene glycol, or butylene glycol. For the first step ATH conversion, it is desirable to employ a water/alcohol solution so that the conversion proceeds cleanly and in good yield. However, while not wishing to be bound by theory, it is believed that the use of a water/alcohol solution in the succeeding second H-T-GP conversion step leads to the formation of a difficult-to-clean tarry residue, which contributes substantially to the overall cost of the process. It is believed that the tar may be formed at least in part as the result of consuming valuable haloenone reactant, principally in the hydroxy form, thereby lowering the yield of gamma pyrone relative to that which would be obtainable if tar formation could be avoided or at least reduced. It is accordingly believed that by conducting the H-T-GP conversion in a dry aprotic solvent as hereinafter further defined, the alkoxy-hydroxy equilibrium depicted in Scheme I is shifted substantially in favor of the alkoxy form III which participates relatively little or not at all in tar formation. Consequently, tar formation can be reduced and yields improved.

It is noted that haloenone III is generally produced as both cis and trans isomers, although the existence of an isomeric mixture does not particularly affect this invention since both isomers lead to the formation of gamma pyrone product. The trans isomer of formula IIIl where R and $R^1$ are methyl can spontaneously crystallize out of solution, depending on the solvent, as illustrated in the examples.

The aprotic solvent reaction medium for the H-T-GP conversion is "dry", meaning that protic solvent components such as water and alcohol(s) (i.e., including $(C_1–C_6)$ alcohols or $(C_2–C_4)$ diols, as discussed below) should constitute less than about 1 equivalent total, per equivalent of haloenone, of the reaction medium. Thus the term "dry", as used herein, refers to a relatively reduced content of all protic solvent components, not just a reduced content of water. It is preferred that the H-T-GP aprotic reaction medium be substantially free of protic solvent components, "substantially free" meaning that less than 0.1 equivalent total of protic solvent components (water plus alcohols and/or diols) are present per equivalent of haloenone.

The haloenone III useful in this invention need not be extracted directly from an ATH water/alcohol reaction medium. Rather, haloenone IIIl can first be isolated from the water/alcohol medium, or derived by any other chemical means known to the art, and then taken through the H-T-GP conversion. Isolation of haloenone III can be effected conventionally, for example by evaporation of solvent followed by vacuum distillation to obtain substantially pure haloenone. It is noted that the specific trans haloenone isomer wherein R and $R^1$ are methyl spontaneously crystallizes from water/alcohol solution. This particular compound can be collected by simple filtration to obtain the crystals, optionally followed by recrystallization from hexane to purify.

If a direct extraction of a water/alcohol ATH reaction medium is employed, it is preferred to conduct the H-T-GP conversion after at least partially removing water and other protic components (such as alcohol) which can carry over from the ATH water/alcohol reaction medium into the aprotic solvent used as the reaction medium for the H-T-GP conversion. It is most preferred to conduct the H-T-GP conversion in an aprotic solvent which is substantially free of both water and alcohol, as noted above. To the extent that water and alcohol which carry over from the ATH conversion are removed from the aprotic solvent which comprises the H-T-GP reaction medium, tar formation can be reduced and yields may be improved. Thus, where haloenone III is made via an ATH conversion process which employs a mixture of water and a $(C_1–C_6)$ alcohol and/or a $(C_2–C_4)$diol as the reaction solvent, this invention further provides a method of synthesizing a compound having the formula

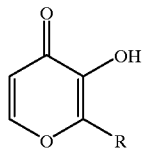

(II)

wherein R is (C$_1$–C$_6$)alkyl, (C$_2$–C$_6$)alkenyl, phenyl, or benzyl, comprising the steps of (A) treating a compound having the formula

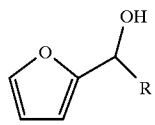

(IV)

wherein R is as defined above, in an aqueous solution containing a (C$_1$–C$_6$)alcohol or a (C$_2$–C$_4$)diol, with a halogen oxidant containing reactive bromine or chlorine, thereby yielding an aqueous solution of a compound having the formula

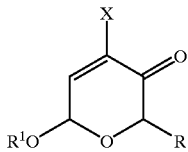

(III)

wherein R$^1$ is (C$_1$–C$_6$)alkyl or hydroxy(C$_2$–C$_4$)alkyl and X is chloro or bromo;

(B) extracting the aqueous solution produced in step (A) with an organic solvent (herein referred to as the extraction solvent), thereby producing a solution comprising said compound III and said organic solvent; and (C) treating said compound III extracted in step (B), at a temperature above about 40° C. and in a dry aprotic solvent, with a catalytically effective amount of acid, thereby effecting conversion of said compound III to said compound II.

In a preferred embodiment, the step (C) aprotic reaction medium is substantially free of water and alcohol.

DETAILED DISCUSSION

The invention is typically practiced by first conducting an ATH conversion as known in the art, see for example any of U.S. Pat. Nos. 4,435,584, 4,323,506, 4,368,331 and 4,387,235. In general, furfuryl alcohol IV is treated with a halogen oxidizing agent in a solution of a lower alcohol or diol in water to make haloenone III. The ratio of water to alcohol is not critical so long as there is sufficient alcohol to satisfy the stoichiometry of the reaction. The water/alcohol ratio typically ranges from about 20:1 to about 1:20 (v/v) with 1:1 being typical.

Methanol is preferred as the alcohol due to its ready availability, low cost, and ease of stripping prior to conducting the H-T-GP conversion, as explained further below. Ethanol and the isomers of propyl alcohol are also preferred because they are miscible with water in all proportions. If a diol is to be employed it is preferred to use a glycol such as ethylene glycol, propylene glycol, or butylene glycol.

Alcohols which form a two-phase system with water are also feasible, the ATH conversion being conducted with the two-phase system. In this two-phase case, however, the haloenone product will be more soluble in the alcohol layer. The haloenone can therefore be advantageously harvested for the H-T-GP step as a residue following separation of the alcohol layer and evaporation of the alcohol, and the residue then added to the aprotic solvent which is to function as the H-T-GP reaction medium. The H-T-GP conversion is then conducted as herein described. No intermediate extraction of the ATH reaction medium need be performed. This mode of practicing the invention is less preferred than when the alcohol employed in the ATH conversion is water-soluble.

Typically at least two equivalents of halogen oxidizing agent are employed in the ATH conversion. The halogen oxidant can be chlorine, bromine, bromine chloride, hypochlorous or hypobromous acid or mixtures thereof. Bromine chloride is a commercially available gas. The halogen oxidant can be added by simply sparging it through the water/alcohol reaction medium. It can also be prepared in situ by the addition of chlorine to a solution of sodium or potassium bromide or by the addition of bromine to a solution of sodium or potassium chloride. Hypochlorous and hypobromous acid can be conveniently generated in situ by the addition of aqueous acid (HCl, H$_2$SO$_4$, HBr, etc.) to a solution of the alkali or alkaline earth metal hypohalite, e.g., NaOCl, KOCl, or Ca(OCl)$_2$. The preferred halogen oxidants, based on cost factors, are chlorine and bromine chloride prepared in situ.

The ATH conversion can be implemented, as known in the art, at a temperature typically from about −50 to about 50° C., preferably at −10 to 10° C., and at ambient pressure in a reaction vessel implemented with suitable venting capability if a halogen gas is to be employed as the halogen oxidant. The reaction time is typically on the order of about one half hour or less, although the reaction can be set to run for anywhere from a few minutes to several hours or even longer if desired.

After conducting the ATH conversion in the water/alcohol reaction medium, the reaction medium can be extracted with any organic solvent which forms a two phase liquid-liquid extraction system with the reaction medium and which has an appreciable differential solubility for the haloenone, relative to the water/alcohol reaction medium, so that the haloenone will partition effectively. The extraction can be conducted by any conventional means such as a separatory funnel. Multiple extractions with fresh extraction solvent can be advantageous. Although not strictly necessary, the extracting solvent can advantageously and conveniently be the same as the aprotic solvent employed for the H-T-GP conversion provided that it forms a two phase extraction system with water/alcohol. Suitable extraction solvents include any of the aprotic solvents mentioned below which form a two-phase system with water, for example, toluene, benzene, any of the o-, m-, or p-xylenes, any of the isomeric saturated (C$_5$–C$_{10}$)alkanes such as the aliphatic hexanes or heptanes, cyclohexane, (C$_2$–C$_4$)alkyl acetates, propionates and butyrates such as ethyl acetate and butyl acetate, (C$_3$–C$_{10}$)ketones such as methyl isobutyl ketone, and any of the di(C$_1$–C$_6$)alkyl ethers representative members of which include diethyl ether, diisopropyl ether or diisobutyl ether. Aprotic solvents which do not form a two-phase system with water (i.e., because they are water-soluble) are not suitable. It may be advantageous to heat the water/alcohol reaction medium and the extraction solvent to facilitate equilibration of partitioning between the phases.

After the extraction is completed the extracting solvent (containing the haloenone) is drawn off or otherwise separated from the ATH water/alcohol reaction medium to conduct the next step. The next step can vary depending on the particular aprotic solvent in which it is desired to conduct the H-T-GP conversion. A first case can arise where the aprotic solvent desired for the H-T-GP conversion is freely soluble in the water/alcohol ATP conversion reaction medium, for example THF, DMSO or glyme, meaning that it is not suitable for use in the extraction step and that a different solvent suitable for extraction will have been employed. In this case, the extraction solvent will first be removed, for example by simple distillation, prior to adding the desired (water-soluble) aprotic solvent to the haloenone-containing residue and conducting the H-T-GP conversion. It is noted for this first case that extraction solvents having low boiling points (e.g., any of the isomeric aliphatic hexanes) are preferred in part due to the ease with which they may be removed by distillation, e.g., by simple rotary evaporation using house vacuum.

A second case can arise where the aprotic solvent desired for use in the H-T-GP conversion also forms a two-phase system with the water/alcohol ATP reaction medium and is also useful as an extraction solvent. Such solvents are preferred in this invention in part because no intermediate distillation step such as that described above is required. Preferred solvents for this case will ideally have low solubility toward water and the alcohol(s) employed in the ATH reaction medium, and will accordingly exhibit little carryover of water and alcohol. A preferred solvent in this category is toluene.

A third case occurs where it is desired to use an H-T-GP aprotic solvent different from the extraction solvent, even though the H-T-GP solvent could itself also function as the extraction solvent. Thus, it may, for example, be desired to employ hexane as the extraction solvent and toluene or an alkyl acetate as the H-T-GP solvent. In this case the extraction solvent (e.g., hexane) will first be removed, for example by evaporation, and aprotic solvent (e.g., toluene) will then be added to the residue.

As previously mentioned, an additional case can arise if no extraction step is employed. Rather, the haloenone can be isolated following the ATH conversion, for example, by evaporation of solvent followed by vacuum distillation, thereby yielding a solvent residue containing the haloenone, or substantially pure haloenone, depending on the extent and/or completeness of evaporation. This residue can be added directly to an aprotic solvent and the H-T-GP conversion effected. This case is less preferred than that in which a direct extraction of the ATH water/alcohol reaction medium is conducted.

Suitable aprotic solvents for use as the reaction medium in which to conduct the H-T-GP conversion include any of those known to the art which are liquid, stable to heat and inert to reaction with the acid employed, including toluene, dioxane, benzene, halobenzenes such as chlorobenzene, any of the isomeric saturated aliphatic ($C_5$–$C_{10}$) alkanes such as the hexanes and heptanes, any of the o-, m-, or p-xylenes, cyclohexane, dimethylsulfoxide (DMSO), nitromethane, tetrahydrofuran (THF), any of the di($C_1$–$C_6$)alkyl ethers representative members of which include diethyl ether, diisopropyl ether or dibutyl ether, ($C_2$–$C_4$)alkyl acetates, propionates, and butyrates such as ethyl acetate and butyl acetate, symmetrical or unsymmetrical ($C_3$–$C_{10}$)ketones such as methyl isobutyl ketone, and any of the methoxy-capped ethylene oxide ethers having the formula

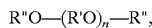

wherein R" is methyl, R' is ethyl, and n is 1–3, representative members of which include glyme, diglyme, and triglyme. Mixtures of one or more of the preceding aprotic solvents are also useful.

One or a mixture of aprotic solvents can be preferred for use in the H-T-GP conversion reaction medium for several reasons. One group of preferred solvents include those which have a boiling point exceeding 100° C. or, if their boiling point is lower, which have a boiling point above the temperature used for the H-T-GP conversion. A specifically preferred solvent in this category is toluene. A second group of preferred solvents includes those aprotic solvents which can be used to extract haloenone and which have relatively low solubility for the water and/or alcohol components of the ATH conversion reaction medium. These solvents can be employed for both the haloenone extraction and for the H-T-GP conversion and result in only a small amount of carryover of water and/or alcohol from the ATH conversion. A third group of aprotic solvents are preferred for their ability to form azeotropes with water, examples of which include toluene and benzene. Toluene and toluene/aprotic co-solvent mixtures, for example solutions of toluene/THF, toluene/diisopropyl ether, toluene/ethyl acetate, and toluene/butyl acetate are especially preferred as aprotic solvents. ($C_2$–$C_4$)alkyl acetates are also especially preferred.

Acids useful as catalysts for conducting the H-T-GP conversion include non-oxidizing strong acids which are catalytically effective to drive or implement the H-T-GP conversion. Generally, any acid which is non-reactive under the conditions employed for the H-T-GP conversion and which have a $pK_a$ in water less than about 3 can be employed. Suitable acids include p-toluenesulfonic acid, methanesulfonic acid, hydrogen fluoride, hydrogen chloride, hydrogen bromide, trifluoroacetic acid, pentafluoropropionic acid, trichloroacetic acid, phosphoric acid, oxalic acid and sulfuric acid. Lewis acids such as $SnCl_4$, $ZnCl_2$, and $TiCl_4$ are also useful in the invention. The acids are employed neat, where possible. Those acids which normally require water as a solvent, such as sulfuric acid, are used in concentrated form.

It is useful for the aprotic solvent to have an appreciable solubility for the particular acid being used. In the event that it is desired to employ HCl or HBr as the acid in combination with a particular solvent which does not dissolve acid to an extent sufficient to induce the H-T-GP conversion to proceed at a desired rate, it may be necessary to conduct the reaction by pressurizing with gaseous HCl or HBr, as explained further below.

As previously stated, the H-T-GP conversion should be conducted in an aprotic solvent which is dry as previously defined. The dry aprotic solvent contains a reduced content of protic solvent components, such other (protic) solvent components generally comprising water and alcohol (and/or a diol) which may have carried over in the extracting solvent from the ATH conversion. If desired, residual (or carryover) water and alcohols can be measured and/or monitored by any of a number of conventional methods well known to the art. Water can be measured by the well known Karl Fisher titrimetric method. Water and individual alcohols or diols can also be measured with gas chromatography.

If necessary, there are a number of ways in which excess residual alcohol(s) and water can be removed, or at least reduced to the point that they constitute less than 1 equivalent, per equivalent of haloenone, of all solvent components constituting the H-T-GP reaction medium, prior to conducting the H-T-GP conversion. It is to be understood that reference to the removal of "alcohol" refers to the removal of any one or more of the ($C_1$–$C_6$)alcohols or ($C_2$–$C_4$)diols which can be used as a reactant/co-solvent in the ATH conversion reaction medium. It is noted that the process of removing water and/or alcohol prior to conducting the H-T-GP conversion is sometimes referred to herein as a "stripping" procedure.

Protic solvent components such as water and alcohol can be removed, prior to adding acid to the aprotic solvent reaction medium and conducting the H-T-GP conversion, by heating the aprotic solvent to the boiling point of the aprotic solvent, or to a temperature below the boiling point of the aprotic solvent but above the temperature at which water and/or alcohol distills off. To effectively strip off water and alcohol by heating at atmospheric pressure, the boiling point of the aprotic solvent should advantageously exceed 100° C. Temperatures lower than 100° C. are also feasible, particularly when the stripping procedure is conducted under vacuum. Temperatures less than 100° C. at atmospheric pressure may also be employed, but removal of water and alcohol may not be complete.

Water and alcohol can also be removed by first treating the aprotic solvent with a drying agent, for example any of the molecular sieves widely known and commercially available for the purpose, or any of the widely known anhydrous salts, for example anhydrous sodium sulfate, which dry out liquids by converting to their hydrated form. Following removal of water with a drying agent, the aprotic solvent can then be heated to a temperature at which residual alcohol distills off, which temperature can be below 100° C. in the case where methanol and/or ethanol are employed.

In the case of some aprotic solvents such as toluene and benzene with which water forms an azeotrope, the solvent can be heated at atmospheric pressure to the temperature (below 100° C.) at which water is removed as a water/solvent azeotrope, followed, if necessary, by heating to distill off residual alcohol.

The above discussion regarding water/alcohol stripping procedures assumes that the aprotic solvent employed for the H-T-GP conversion is also used as the extraction solvent for the ATH reaction medium following the ATH conversion. Those skilled in the art will appreciate that in the event that the extraction solvent and the H-T-GP aprotic conversion solvent are different, it then is possible to conduct any of the above-discussed stripping procedures on either the ATH extraction solvent, on the H-T-GP conversion solvent, or on both, as appropriate.

As previously mentioned, for the ATH conversion methanol is preferred as the alcohol co-solvent due in part to its ready availability and cheap price. It is also preferred due to the ease with which it can subsequently be stripped from the extraction solvent. Ethanol is also readily stripped and is accordingly also preferred.

The aprotic reaction medium, which is now dry, and preferably substantially free of water and alcohol, can be treated with a quantity of acid catalytically sufficient to effect the H-T-GP conversion. The acid can advantageously be used in excess, for example in an amount of 2–5 equivalents of acid per equivalent of haloenone. While higher ratios of acid to haloenone are also feasible, such are not preferred. Acids such as trifluoroacetic acid and trichloroacetic acid are desirable due to their good solubility in organic aprotic solvents of the type useful in this invention. If a gaseous mineral acid such as HBr or HCl is employed, the H-T-GP conversion need not be conducted under pressure so long as the aprotic solvent employed has sufficient solubility for the acid, e.g., an aprotic solvent such as any of the glymes (glyme, diglyme, or triglyme). In the event that it is desired to employ HCl or HBr as the acid and also to employ an aprotic solvent which has low solubility for these particular acids, it is possible to conduct the H-T-GP conversion at an elevated temperature, for example 80–120° C. while sparging HCl or HBr through the aprotic reaction medium. It can also be useful to conduct the H-T-GP conversion under pressure of HCl and/or HBr. The use of pressure in this situation generally results in an increased yield of the desired gamma pyrone relative to the yield achievable without employing pressure and represents a preferred embodiment. An initial pressure may be established at 10–15 pounds per square inch (psi) [69 to 103.5 milliPascals, mPa] above ambient by simply inletting gaseous HBr or HCl into an otherwise closed or sealed reaction vessel. The pressure can then be increased by closing off the gas inlet and heating. This represents the preferred mode of generating pressure—establishing a desired threshold pressure with HCl or HBr gas and then closing off the system and heating until the desired pressure is reached. In general, the higher the pressure which is employed, the better the yield of gamma pyrone will be. Thus the pressure can, if desired, be increased to whatever level is desired consistent with safety specifications for the particular reaction vessel and equipment being employed. In general, in order to avoid having to employ equipment with high pressure safety limits, it is preferred to employ a pressure within the range of about 50 to about 500 psi [345 to 3450 mPa], preferably 50 to 150 [345 to 1035 mPa] psi.

The H-T-GP conversion is usually allowed to proceed substantially to completion, typical reaction times being 0.5 to 6 hours when operating within the preferred temperature range of 80–120° C. The final gamma pyrone product can be isolated conventionally by solvent evaporation followed, if desired, by recrystallization from water, methanol, or a combination thereof. Progress of the reaction can be monitored conventionally, e.g., by high performance liquid chromatography, for example using a C-18 column in reverse phase mode with acetonitrile containing phosphate buffer as the isocratic eluant, with proportions being adjusted to get optimum resolution. Generally, the pH of the eluant will range between about 2.2 and 7.4. If it is desired to stop the reaction prior to completion, the final gamma pyrone product can be separated from residual haloenone conventionally, for example, by column chromatography over silica gel.

The invention will now be further explained and illustrated by means of the following examples which are not to be taken as limiting.

EXAMPLE 1

This Example illustrates a process according to the invention using a commercially obtainable furfuryl alcohol as the starting material.

Example 1a—Formation of Haloenone III (ATH Conversion)

A glass lined reactor was charged with 32.7 Kg of water and 49.4 Kg of methanol and chilled to −5° C. with stirring. Ethyl furfuryl alcohol (IV, R=Ethyl, 17.8 kg, 97.2% pure, obtained from Quaker Oats) and chlorine (19.9 kg) were added concomitantly into the reactor at a rate such that the temperature was maintained at −5° to 0° C. This resulted in the ethyl furfuryl alcohol starting material being essentially completely consumed as monitored by high performance liquid chromatography (HPLC) using a C-18 column (Waters, Division of Millipore) reverse phase with, as isocratic mobile phase, 400 mL methanol, 600 mL distilled water, and 20 mL acetonitrile, final pH adjusted to 2.2 with 85% phosphoric acid (J. T. Baker). The aqueous alcoholic solution of product (formula III, $R^1$=methyl, R=ethyl) was employed as the starting material reaction mixture for Example 1b.

Example 1b —Extraction of Haloenone III into aprotic solvent

A total of 1199 g of the reaction mixture from Example 1a was charged into a 2-liter 3-necked flask followed by 400 g of toluene, thereby forming a two-phase extraction mixture. The mixture was heated at 60–65° C. for 4 hours with stirring to extract the haloenone III ($R^1$=Methyl, R=Ethyl). The toluene layer was separated and the aqueous layer was heated with 200 g of fresh toluene for an additional hour to complete the extraction. The toluene layers were combined and washed with 500 mL of a 5% $NaHCO_3$ solution and then dried over $MgSO_4$. This toluene extract contained haloenone III as a mixture of cis and trans isomers.

Example 1c—Formation of gamma pyrone (H-T-GP Conversion)

A 100 mL round-bottomed flask was charged with 34.8 g of the toluene extract from Example 1b. Methanol and toluene were distilled off under vacuum (~100 mm Hg) from the extract at bath temperature <40° C. until about 15 g of material remained. The remaining concentrated toluene solution was then transferred to a reactor capable of carrying out reaction under pressure. Fresh, dry toluene was added to the reactor until the total weight was 55 g. Anhydrous HCl gas (5.0 g) was then metered into the reactor under pressure. With stirring, the reaction mixture was heated for 2 hours at ~100° C. during which the pressure increased to ~110 psi. After the reaction was complete, the reactor was cooled, excess HCl vented and the reaction mixture was assayed by HPLC for the amount of ethyl maltol (II, R=Ethyl) (compared to a standard ethyl maltol solution of known concentration). The yield of II (R=ethyl) was found to be 72% based on amount of ethyl furfuryl alcohol ((IV, R=Ethyl) as stated in Example 1a. The final solution of ethyl maltol was dark; however, tar did not form in an amount sufficient to be occluded from solution.

EXAMPLE 2

Conventional Process

This example illustrates the formation of a gamma pyrone by using a conventional process which employs an aqueous alcohol reaction medium, rather than extracting the haloenone intermediate into a medium comprising an aprotic solvent according to the invention.

A portion of an aqueous alcohol mixture containing haloenone, generated as in Example 1a, was converted to ethyl maltol (II, R=Ethyl) by heating the aqueous mixture at 85° C.–100° C. for 3 hours. The acid employed to convert the haloenone to ethyl maltol was HCl generated in situ as a by-product from the furfuryl alcohol chlorination. No additional HCl or other acid was added. Substantial amounts of tar formed, particularly in comparison with Example 1, and were visibly present in the reaction vessel. The yield of ethyl maltol (II, R=Ethyl) by HPLC was 69% based on ethyl furfuryl alcohol (IV, R=Ethyl).

EXAMPLE 3

Example 3a—Formation of Haloenone (ATH Conversion)

The same procedure as in Example 1a was employed for reacting methyl furfuryl alcohol (IV, R=Methyl, obtained from Quaker Oats) with chlorine in a water/methanol solution. This mixture is referred to below as a "chlorination mixture".

Example 3b—Extraction of trans-isomer into medium comprising aprotic solvent

The same procedure as in Example 1b was employed to produce a toluene extract of haloenone III ($R^1$=R=Methyl) from the aqueous haloenone-containing mixture produced in Example 3a. If desired, the trans isomer of III ($R^1$=R=Methyl) could be isolated as white crystalline needles from the chlorination mixture by allowing the solution to stand at 0° to –10° C. for several hours and, for the sake of convenience, the trans isomer was isolated in this case.

Example 3c

Anhydrous HCL gas (4.0 g, 109.5 mmol) was metered into a solution of pure trans methyl methoxychloroenone (III, $R^1$=R=Methyl, 5.0 9, 28.5 mmol) (trans-MMCE) in 50 g of dry toluene in a reactor. With stirring, the mixture was heated for 2 hours at 100° C. The yield of maltol (I), based on the trans isomer, was 83% by HPLC assay.

EXAMPLE 4

Comparison Example

As a comparison with Example 3 which illustrates the benefit of employing an anhydrous, aprotic solvent as the H-T-GP reaction medium, pure trans methyl methoxychloroenone produced as in Example 3b was reacted in a mixture containing 50% methanol and 50% concentrated hydrochloric acid at 100° C. for 2 hours. The yield of maltol (I) was 73% by HPLC assay.

EXAMPLE 5

The same procedure as in Example 3c was employed using trans-MMCE except that a solvent mixture containing 80% toluene and 20% tetrahydofuran was used. The yield of maltol (I) was 88% based on the amount of trans-MMCE starting material.

EXAMPLE 6

The same procedure as in Example 3c was employed using trans-MMCE but diglyme was used as solvent. The yield of maltol (I) was 89.3%.

EXAMPLES 7–25

A number of H-T-GP conversions were conducted using the trans MMCE isomer isolated as in Example 3c as starting material, and are reported in Table 1. The column heading "Pressure" indicates the pressure of acid employed at the temperature indicated, with the pressure being atmospheric where the acid either was a liquid to begin with $TiCl_4$, trichloroacetic, or concentrated sulfuric) or was freely soluble in the solvent indicated as the reaction medium. Where a solvent mixture is indicated, the ratio of solvents was 4/1 by weight, respectively. The reaction was monitored by HPLC and considered complete when the trans-MMCE isomer peak had receded essentially to baseline and, correspondingly, when the product gamma pyrone peak had leveled off. Generally, the reaction period varied from about two to about five hours.

TABLE 1

| Solvents | Acid | Temperature (°C.) | (Pressure, psi) [Pressure, milliPascals] | Yield (%) |
|---|---|---|---|---|
| Dioxane | HCl | 98 | (65 psi) [448 mPa] | 76 |
| DMSO | HCl | 83 | Atmospheric | 92.5 |
| Nitromethane | HCl | 80 | Atmospheric | 88 |
| $CH_2Cl_2$ | HCl | 99 | (170) | 78 |

TABLE 1-continued

| Solvents | Acid | Temperature (°C.) | (Pressure, psi) [Pressure, milliPascals] | Yield (%) |
|---|---|---|---|---|
| MIBK | HCl | 99 | (80) [1173] [552] | 73.5 |
| n-Propyl Acetate | HCl | 100 | Atmospheric | 66 |
| DMSO | $H_2SO_4$ | 80 | Atmospheric | 88 |
| DMSO | $TiCl_4$ | 80 | Atmospheric | 83 |
| 1,1,1,2-Tetrachloroethane | HCl | 100 | (150) [1035] | 57 |
| Chlorobenzene | HCl | 100 | Atmospheric | 54 |
| DMF | HCl | 80 | Atmospheric | 69 |
| m-Xylene | HCl | 100 | (125) [862] | 65 |
| Glyme | HCl | 80 | Atmospheric | 87 |
| Isopropyl Ether | HCl | 100 | (65) [448] | 55 |
| Toluene/ Isopropyl Ether | HCl | 100 | (120) [828] | 87 |
| Dibutyl Ether | HCl | 100 | (100) [690] | 87 |
| Toluene/ Methyl t-Butyl Ether | HCl | 100 | (65) [448] | 81 |
| Diglyme | $H_2SO_4$ | 100 | Atmospheric | 81 |
| Toluene | $CCl_3COOH$ | 100 | Atmospheric | 86 |

EXAMPLE 26

Example 26a—Formation of Haloenone III (ATH Conversion)

Example 1a was followed, substituting 12.54 kg of pure methylfurfuryl alcohol (IV, R=methyl) for ethylfurfuryl alcohol, with 15.90 kg total of chlorine added.

Example 26b—Extraction of Haloenone III into aprotic solvent

A fresh portion of the chlorination mixture (400.0 gm) from Example 26a kept at −20 to −10° C. was added to a well stirred 60° C. two phase mixture of 400.0 gm of toluene, 58.0 gm of concentrated HCl, 22.0 gm of water, and 60.0 gm of methanol over two hours. The mixture was allowed to stir at 60° C. for 1 hour. The layers were separated, and the bottom aqueous layer was extracted twice with 100 ml portions of methylene chloride. The organic layers were combined and concentrated to about 50 ml on the rotary evaporator. Dry toluene (250 ml) was added and the material reconcentrated to about 50 ml. This procedure was repeated three times to remove any residual water, The resulting dry extract was diluted to 200.0 gm with dry toluene. HPLC analysis indicated an 86.9% yield of methylmethoxychloroenone (III, $R_1$ $R_1$=methyl, X=Cl) from methylfurfuryl alcohol IV.

Example 26c—Formation of gamma pyrone (HTGP conversion)

A 100 ml Teflon reaction bomb was charged with 50.0 gm of the toluene extract from example 26b, 12.5 gm of dry ethyl acetate, and 5 gm of anhydrous gaseous HCl. The bomb was sealed and the reaction was heated at 100° C. for 2 hours. The reactor was then cooled, and the contents dissolved in methanol. HPLC analysis indicated a 92.8% yield of maltol (I) from methylmethoxychloroenone III and an overall yield of 80.7% from methylfurfuryl alcohol IV.

EXAMPLE 27

Hydrolysis of Example 26a According to Prior Art Methodology

This Example illustrates the formation of a gamma pyrone by using a conventional process using the same starting material as that used for Example 26. A 3-necked round bottom flask equipped with a short path distillation head and receiver was charged with 20.0 gm of chlorination mixture from example 26a. The flask was heated for 2 hours at 85° C., 10 min. at 95° C., and 10 min. at 100° C. The resulting slurry was dissolved in methanol. HPLC analysis indicated a 55.7% yield of maltol from methylfurfuryl alcohol IV.

EXAMPLE 28

A one liter portion of the reaction mixture from example 1a is added to a 55° C. solution of 1 liter of hexane, 50 ml of concentrated HCl, and 50 ml of methanol over 4 hours. The layers are separated, and the aqueous phase is then continuously extracted with hexane for 2 hours more. The combined hexane layers are evaporated to a yellow oil under reduced pressure. Anhydrous butyl acetate (1 liter) is added, followed by 127 gm of anhydrous HCl gas. With stirring, the reaction mixture is heated to 80° C. for 2 hours, during which time the pressure increases to about 40 PSI. After the reaction is complete, the reactor is cooled, excess HCl is vented, and the reaction mixture is quenched with about 350 gm of 50% aqueous potassium hydroxide, to obtain a pH of about 10.0. The layers are separated, and the organic layer is evaporated under reduced pressure to yield crude ethyl maltol (II).

EXAMPLE 29

A reaction is run as described for Example 28, except isopropanol is used instead of methanol in the formation of the haloenone (ATH converstion), and isopropyl acetate is used instead of butyl acetate in the formation of the gamma pyrone (HTGP conversion).

What is claimed is:

1. A method of making a compound having the formula

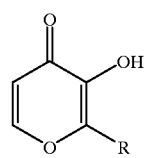

(II)

wherein R is $(C_1-C_6)$alkyl, $(C_2-C_6)$alkenyl, phenyl, or benzyl, comprising treating, at a temperature above about 40° C. and in a dry aprotic solvent, a compound having the formula

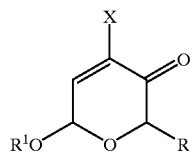

(III)

wherein R is as defined above, $R^1$ is $(C_1-C_6)$alkyl or hydroxy$(C_2-C_4)$alkyl, and X is chloro or bromo, with a catalytically effective amount of acid.

2. A method as defined in claim 1, wherein said temperature is at least about 60° C.

3. A method as defined in claim 2, wherein said temperature is in the range of from about 80° C. to about 120° C.

4. A method as defined in claim 1, wherein said aprotic solvent is substantially free of protic solvent components.

5. A method as defined in claim 1, wherein said aprotic solvent is selected from toluene, dioxane, benzene, halobenzenes, any of the o-, m-, or p-xylenes, any of the isomeric aliphatic ($C_5$–$C_{10}$)alkanes, cyclohexane, dimethylsulfoxide, nitromethane, tetrahydrofuran, any of the di($C_1$–$C_6$)alkyl ethers, ($C_2$–$C_4$)alkyl acetates, propionates and butyrates, ($C_3$–$C_{10}$)ketones, and any of the methoxy capped ethylene oxide ethers having the formula

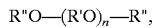

wherein R" is methyl, R' is ethyl, and n is 1–3.

6. A method as defined in claim 5, wherein said aprotic solvent is toluene or a solution of toluene and an aprotic co-solvent.

7. A method as defined in claim 5, wherein said aprotic solvent is a ($C_2$–$C_4$)alkyl acetate.

8. A method of synthesizing a compound having the formula

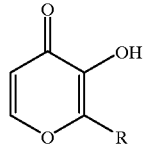

(II)

wherein R is ($C_1$–$C_6$)alkyl, ($C_2$–$C_6$)alkenyl, phenyl, or benzyl, comprising (A) treating a compound having the formula

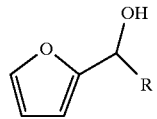

(IV)

wherein R is as defined above, in an aqueous solution containing a ($C_1$–$C_6$)alcohol or a ($C_2$–$C_4$)diol, with a halogen oxidant containing reactive bromine or chlorine, thereby yielding an aqueous solution of a compound having the formula

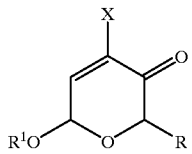

(III)

wherein $R^1$ is ($C_1$–$C_6$)alkyl or hydroxy($C_2$–$C_4$)alkyl and X is chloro or bromo;

(B) extracting the aqueous solution produced in step (A), thereby producing a solution comprising said compound IIII in an extracting solvent; and (C) treating said compound IIII extracted in step (B), at a temperature above about 40° C. and in a dry aprotic solvent, with a catalytically effective amount of acid.

9. A method as defined in claim 8, wherein said temperature is at least about 60° C.

10. A method as defined in claim 9, wherein said temperature is in the range of from about 80° C. to about 120° C.

11. A method as defined in claim 8, wherein said aprotic solvent is substantially free of protic solvent components.

12. A method as defined in claim 8, wherein said aprotic solvent is selected from toluene, dioxane, benzene, any of the o-, m-, or p-xylenes, any of the isomeric aliphatic ($C_5$–$C_{10}$)alkanes, cyclohexane, dimethylsulfoxide, nitromethane, tetrahydrofuran, any of the di($C_1$–$C_6$)alkyl ethers, ($C_2$–$C_4$)alkyl acetates, propionates, and butyrates, ($C_3$–$C_{10}$) ketones, and any of the methoxy-capped ethylene oxide ethers having the formula

wherein R" is methyl, R' is ethyl, and n is 1–3.

13. A method as defined in claim 12, wherein said aprotic solvent is toluene or a solution of toluene and an aprotic co-solvent.

14. A method as defined in claim 12, wherein said aprotic solvent is a ($C_2$–$C_4$)alkyl acetate.

15. A method as defined in claim 8, wherein the extracting solvent employed in said step (B) is the same as the aprotic solvent employed in said step (C).

16. A method as defined in claim 8, wherein the extraction solvent employed in said step (B) is different than the aprotic solvent employed in said step (C).

17. A method as defined in claim 16, wherein the extraction solvent is hexane and the aprotic solvent is a ($C_2$–$C_4$) alkyl acetate.

18. A method as defined in claim 15, wherein each of said extracting and aprotic solvents is toluene.

* * * * *